United States Patent [19]
Gilbert et al.

[11] Patent Number: 5,904,688
[45] Date of Patent: May 18, 1999

[54] ORTHOPAEDIC ASSEMBLY INCLUDING AN ACETABULAR CUP AND CUP INSERTER

[75] Inventors: Stephen G. Gilbert, West Chester, Pa.; Rodney L. Bays, Pierceton, Ind.; Billy N. Sisk, Claypool, Ind.; Richard A. Lane, Fort Wayne, Ind.

[73] Assignee: Bristol-Myers Squibb Co., New York, N.Y.

[21] Appl. No.: 09/001,214

[22] Filed: Dec. 30, 1997

[51] Int. Cl.$^6$ ........................................... A61F 5/04
[52] U.S. Cl. ................. 606/86; 606/81; 606/91; 606/99; 623/22
[58] Field of Search ................. 606/86, 81, 91, 606/99, 53; 623/22, 23

[56] References Cited

U.S. PATENT DOCUMENTS

| | | | |
|---|---|---|---|
| 3,685,058 | 8/1972 | Tronzo | 3/1 |
| 3,859,992 | 1/1975 | Amstutz | 128/92 E |
| 3,874,003 | 4/1975 | Moser et al. | 3/1 |
| 4,305,394 | 12/1981 | Bertuch, Jr. | 128/303 R |
| 4,399,813 | 8/1983 | Barber | 128/92 EC |
| 4,475,549 | 10/1984 | Oh | 128/303 R |
| 4,632,111 | 12/1986 | Roche | 128/303 R |
| 4,662,891 | 5/1987 | Noiles | 623/22 |
| 4,677,972 | 7/1987 | Tornier | 128/92 V |
| 4,716,894 | 1/1988 | Lazzeri et al. | 128/92 V |
| 4,878,918 | 11/1989 | Tari et al. | 623/22 |
| 4,994,064 | 2/1991 | Aboczky | 606/91 |
| 5,030,221 | 7/1991 | Buechel et al. | 606/91 |
| 5,037,424 | 8/1991 | Aboczsky | 606/91 |
| 5,061,270 | 10/1991 | Aboczky | 606/91 |
| 5,098,437 | 3/1992 | Kashuba et al. | 606/89 |
| 5,108,448 | 4/1992 | Gautier | 623/22 |
| 5,108,452 | 4/1992 | Fallin | 623/23 |
| 5,116,339 | 5/1992 | Glock | 606/91 |
| 5,169,399 | 12/1992 | Ryland et al. | 606/91 |
| 5,171,243 | 12/1992 | Kashuba et al. | 606/86 |
| 5,217,499 | 6/1993 | Shelley | 623/22 |
| 5,250,051 | 10/1993 | Maryan | 606/91 |
| 5,261,915 | 11/1993 | Durlacher et al. | 606/85 |
| 5,284,483 | 2/1994 | Johnson et al. | 606/86 |
| 5,320,625 | 6/1994 | Bertin | 606/91 |
| 5,344,461 | 9/1994 | Phlipot | 623/20 |
| 5,364,403 | 11/1994 | Petersen et al. | 606/91 |
| 5,458,637 | 10/1995 | Hayes | 623/16 |
| 5,499,985 | 3/1996 | Hein et al. | 606/99 |
| 5,507,748 | 4/1996 | Sheehan et al. | 606/94 |

FOREIGN PATENT DOCUMENTS

| | | |
|---|---|---|
| 0 147 339 A2 | 7/1985 | European Pat. Off. . |
| 0 357 270 A1 | 3/1990 | European Pat. Off. . |
| 0 470 912 B1 | 5/1995 | European Pat. Off. . |

OTHER PUBLICATIONS

Zimmer, Inc.—Acetabular Components—pp. A99, A102, A110, A116—Literature No. 97–5000–323—c1993.

Zimmer, Inc.—Sheehan Acetabular Cement Restrictor—Literature No. 00–9260–804–00—c1992.

*Primary Examiner*—Michael Buiz
*Assistant Examiner*—David O. Reip
*Attorney, Agent, or Firm*—Margaret L. Geringer

[57] ABSTRACT

An orthopaedic assembly includes a first portion or an acetabular cup and a second connecting portion or a cup inserter. The acetabular cup includes a cavity for receiving a femoral head and a pole defining a longitudinal axis through the cavity. The acetabular cup further includes an annular face which bounds the cavity and has a plurality of notches extending therein. Each notch includes an undercut wall. The annular face further includes a projection receiving device. A cup inserter includes a body with an end face and a plurality of fingers extending from the end face. Each finger is insertable into a corresponding one of the notches in a direction parallel to the longitudinal axis and is rotatable around the longitudinal axis to a locking position. Each finger includes a transverse surface which matingly engages with a corresponding one of the undercut walls when the finger is in the locking position. The cup inserter further includes a projection and a biasing device. The projection is slidably carried within the body and is movable between a retracted position and an extended position. The biasing device biases the projection toward the extended position. The projection is biased to the extended position and received within the projection receiving device of the cup when each finger is in the locking position.

17 Claims, 5 Drawing Sheets

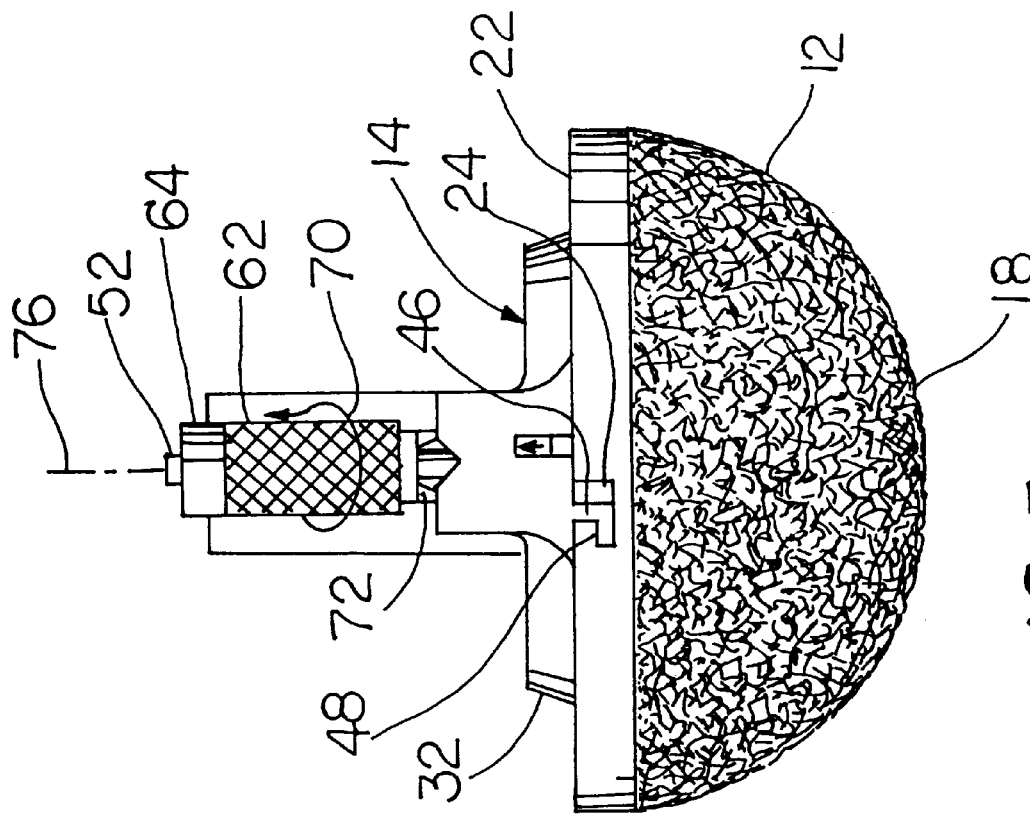
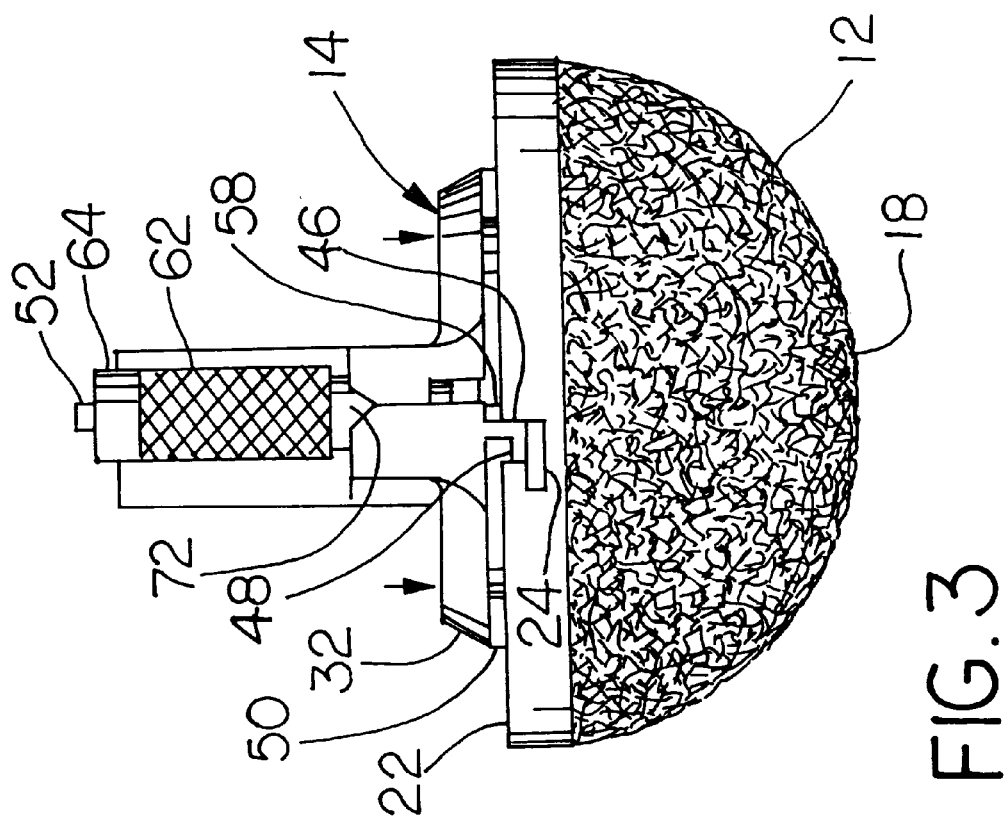

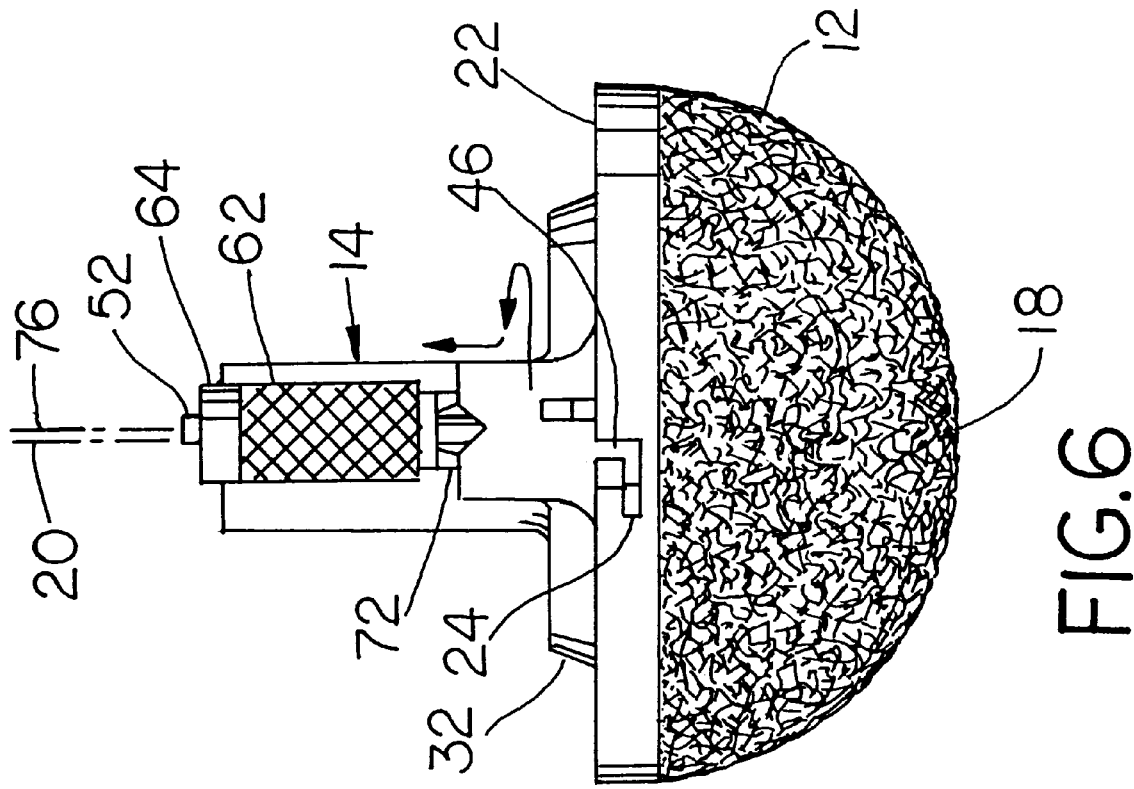
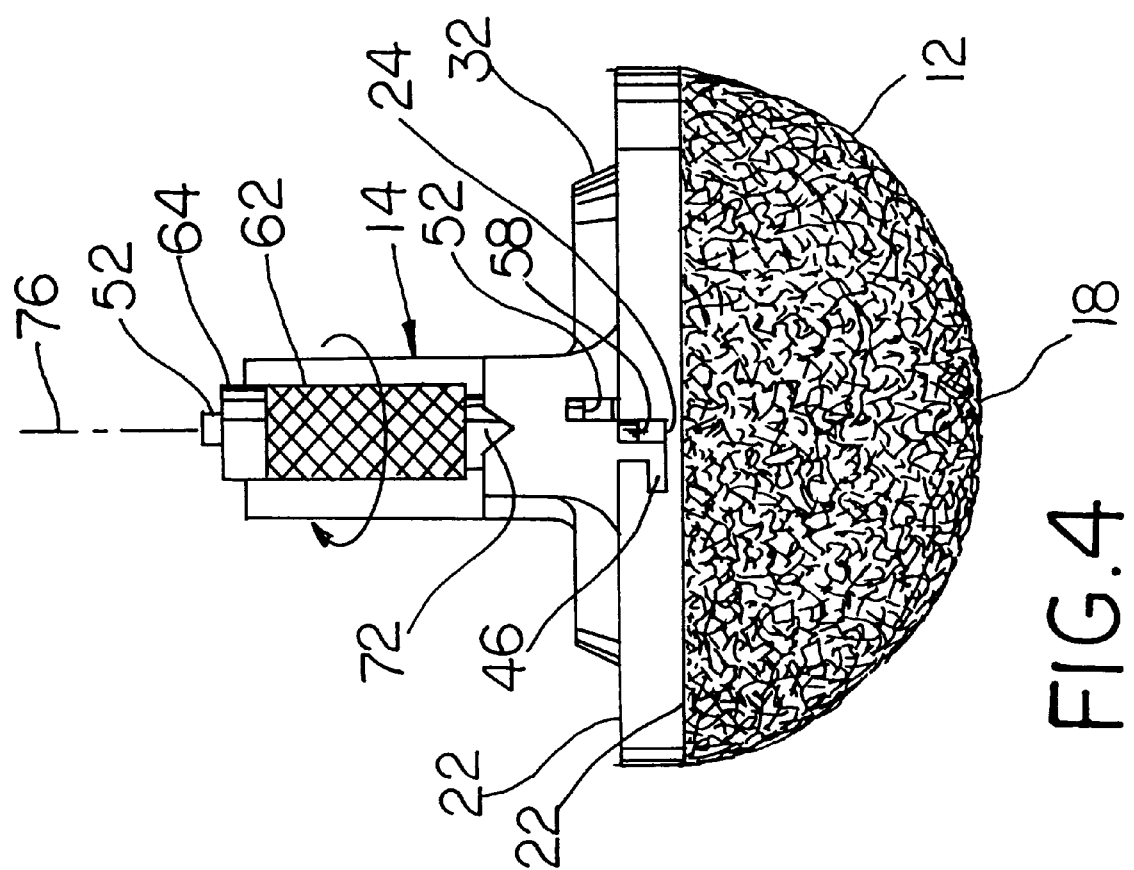

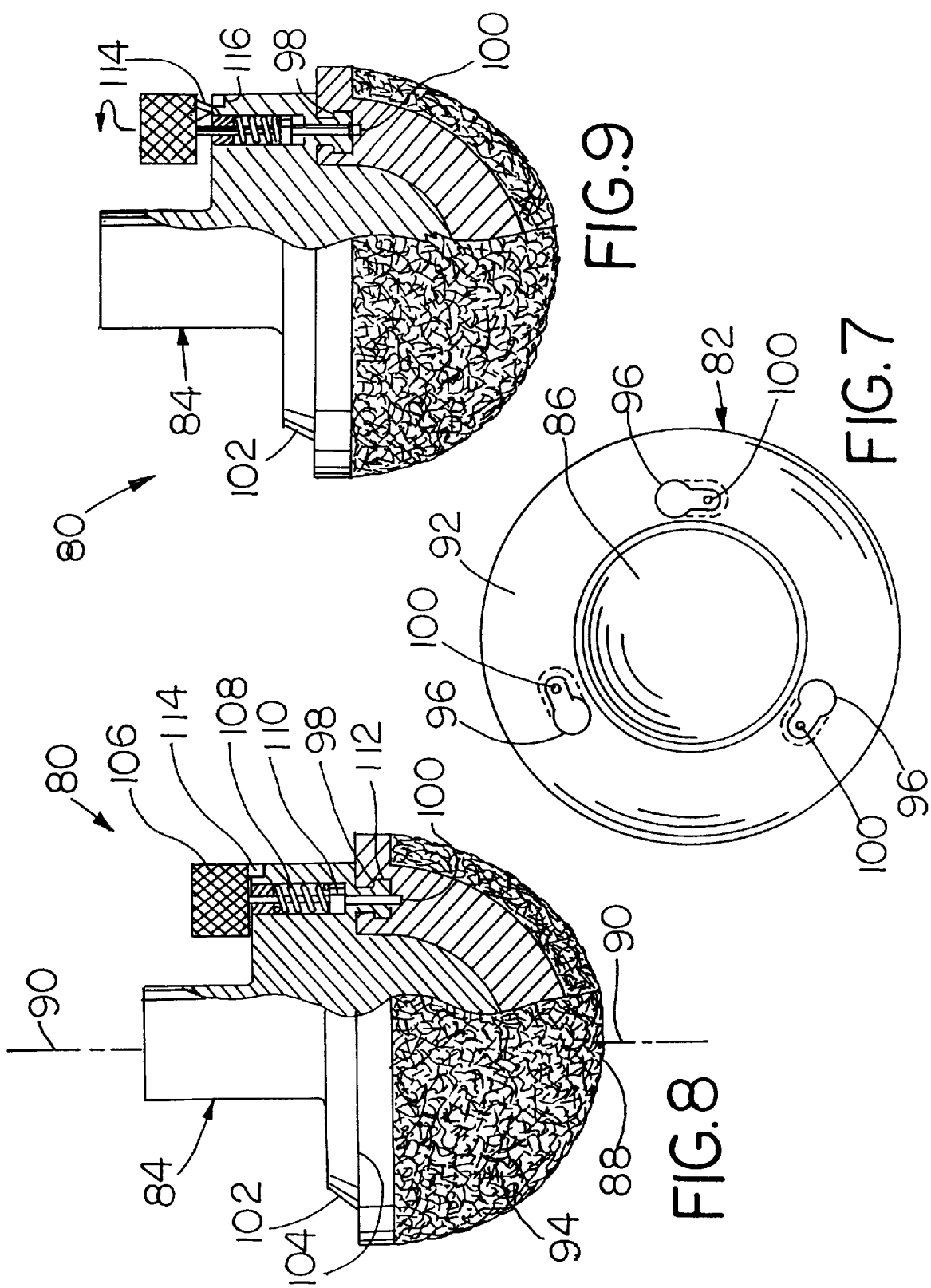

ORTHOPAEDIC ASSEMBLY INCLUDING AN ACETABULAR CUP AND CUP INSERTER

BACKGROUND OF THE INVENTION

1. FIELD OF THE INVENTION

The present invention relates to an orthopaedic assembly, and, more particularly, to an acetabular cup and associated cup inserter used during orthopaedic surgery.

2. DESCRIPTION OF THE RELATED ART

An orthopaedic implant assembly in the form of an acetabular cup is implanted within an acetabulum of a patient. Typically, a cup inserter is attached to the acetabular cup and used to insert and position the cup within the acetabulum. If the acetabular cup includes an outer metallic shell, it is known to form a threaded opening in the pole portion of the shell and thread an end of the cup inserter into the threaded opening. Upon implanting the shell within the acetabulum, the cup inserter is detached from the threaded opening, and then an inner bearing insert is typically assembled to the outer shell forming an acetabular cup assembly.

It is also known to engage the rim of an acetabular cup with a cup inserter for placement of the cup within an acetabulum. For example, U.S. Pat. No. 4,677,972 (Tornier), discloses a cup inserter having a plurality of wedge-shaped teeth which fit within corresponding openings in the rim of an acetabular cup. After the wedged-shaped teeth are placed within the openings in the rim of the cup, the handle of the inserter is moved toward the cup, thereby pushing a plurality of shims into each opening at a location adjacent to each respective wedge-shaped tooth. The shims prevent the wedge-shaped teeth from disengaging the openings in the cup, thereby allowing the cup to be positioned in the acetabulum with the inserter.

SUMMARY OF THE INVENTION

The present invention provides a cup inserter having a plurality of fingers which grip corresponding notches in an annular face on an acetabular cup. The cup inserter includes a finger grip with a spring biasing device which biases a projection into an opening in the annular face of the cup. When received within the opening of the cup, the projection locks the fingers within the notches of the cup. The projection receiving opening may be defined by one of the notches.

The invention comprises, in one form thereof, an orthopaedic assembly including an acetabular cup and a cup inserter. The acetabular cup includes a cavity for receiving a femoral head and a pole defining a longitudinal axis through the cavity. The acetabular cup further includes an annular face which bounds the cavity and has a plurality of notches extending therein. Each notch includes an undercut wall. The annular face further includes a projection receiving device. A cup inserter includes a body with an end face and a plurality of fingers extending from the end face. Each finger is insertable into a corresponding one of the notches in a direction parallel to the longitudinal axis and is rotatable around the longitudinal axis to a locking position. Each finger includes a transverse surface which matingly engages with a corresponding one of the undercut walls when the finger is in the locking position. The cup inserter further includes a projection and a biasing device. The projection is slidably carried within the body and is movable between a retracted position and an extended position. The biasing device biases the projection toward the extended position. The projection is biased to the extended position and received within the projection receiving device of the cup when each finger is in the locking position.

An advantage of the present invention is that the cup inserter may be more easily assembled with the acetabular cup.

Another advantage is that the cup inserter snap locks with the acetabular cup to ensure a positive interconnection therebetween.

Yet another advantage is that an audible click is provided to indicate that the cup inserter has positively interconnected with the acetabular cup.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 3 illustrates the cup inserter of FIG. 1 placed against the acetabular cup;

FIG. 4 illustrates the cup inserter of FIG. 3 with a finger shown received within a notch in the acetabular cup and rotated to a locking position, and a projection received within the same notch;

FIG. 5 shows the cup inserter of FIG. 4, with the finger grip rotated to a raised position and the projection in a retracted position;

FIG. 6 shows the cup inserter of FIG. 5, with the finger grip in the raised position and the finger rotated to an unlocked position;

FIG. 7 is a top view of another embodiment of an acetabular cup of the present invention;

FIG. 8 is a fragmentary, side view of another embodiment of a cup inserter of the present invention, when connected with and having a projection received within a notch in the acetabular cup of FIG. 7; and FIG. 9 is a fragmentary, side view of the cup inserter and acetabular cup of FIG. 8, with the finger grip in a raised position and the projection in a retracted position.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
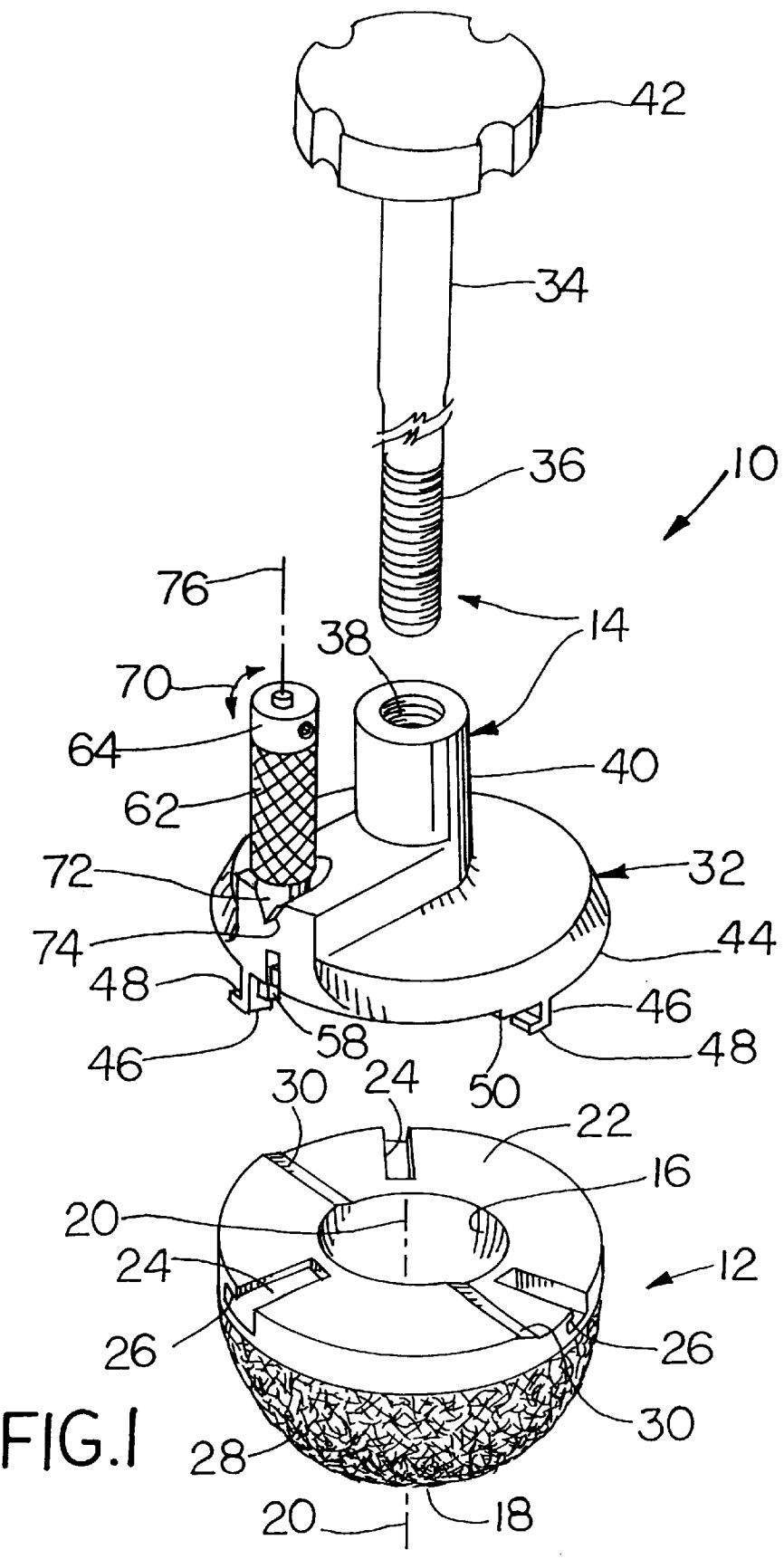
FIG. 1 is a perspective view of one embodiment of an orthopaedic assembly of the present invention, including a cup inserter and an acetabular cup.
Figure 2:
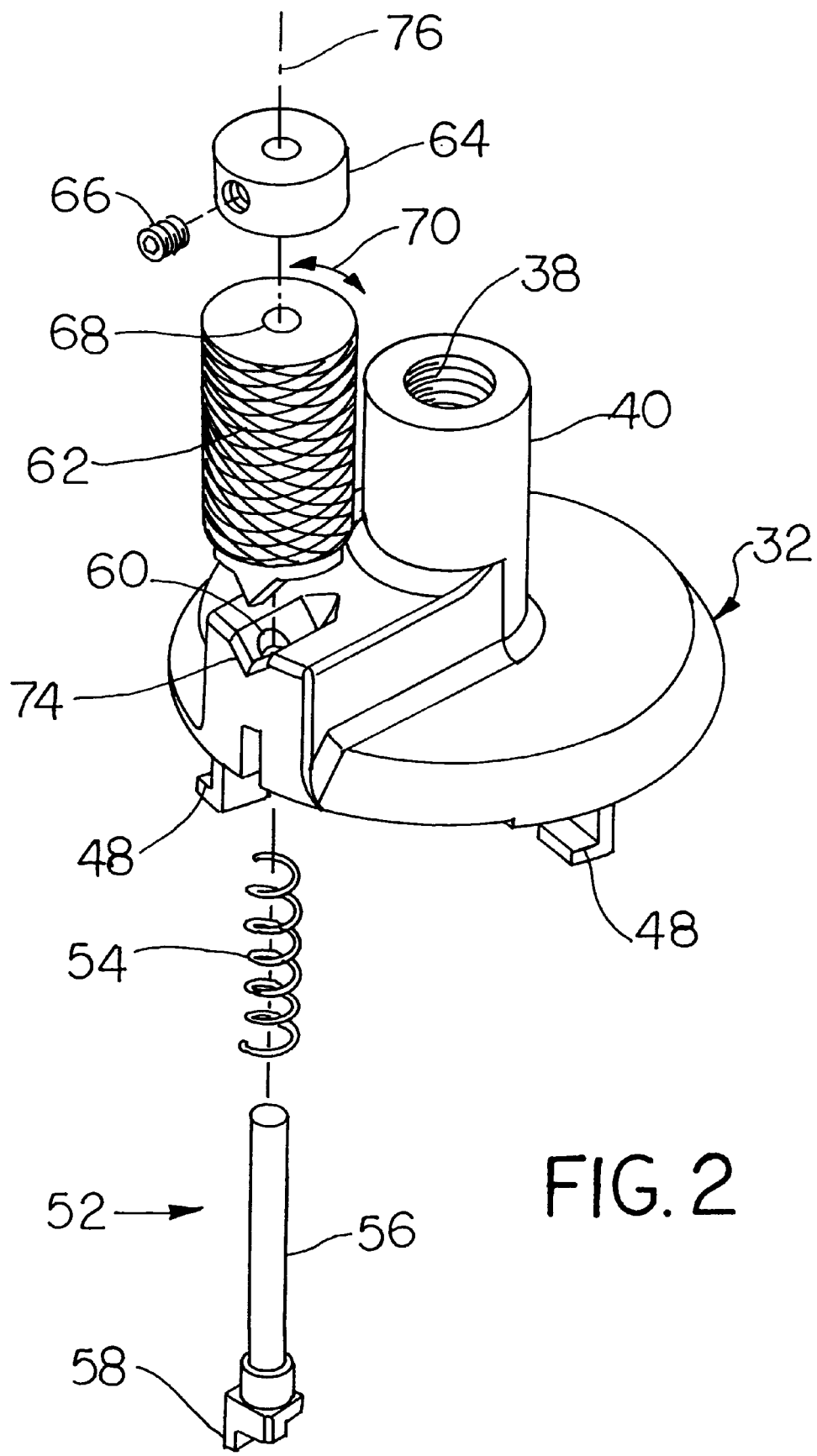
FIG. 2 is a partial, exploded view of the cup inserter shown in FIG. 1.

Referring now to the drawings and more particularly to FIGS. 1 and 2, there is shown an embodiment of an orthopaedic assembly 10 of the present invention, including an acetabular cup 12 and a cup inserter 14. The invention will be described with reference to an acetabular cup and a cup inserter; however, it is understood that the principles of the invention are applicable to any suitable orthopaedic assembly.

A first portion or acetabular cup 12 includes a cavity 16 for receiving a femoral head (not shown) therein. Cup 12 also includes a pole 18 defining a longitudinal axis 20 which extends through an axis of symmetry of cavity 16. Cup 12 further includes an outer or annular face 22 which is disposed at an end opposite pole 18. Annular face 22 bounds cavity 16, and includes a plurality of notches 24 which extend therein. Each notch 24 includes a portion or wall thereof which extends transverse to longitudinal axis 20. In the embodiment shown, each notch 24 includes an undercut wall 26 which extends transverse to longitudinal axis 20 and substantially parallel to annular face 22. Each notch 24 thus has an L-shaped cross section.

In the embodiment shown, cup 12 is formed from a polymeric material, such as ultra-high-molecular weight polyethylene. A porous, metallic shell in the form of a fiber metal shell 28 surrounds the polymeric material and provides a surface for bony ingrowth and/or anchoring of bone cement. However, it is to be understood that cup 12 may be formed as an all polymeric cup, an all metal cup, or any other suitable material or combination thereof which is suitable for a particular application. Any suitable manufacturing methods may be used for cup 12.

Annular face 22 of cup 12 also includes an elevation 30. Elevation 30 provides keyed interconnection with cup inserter 14 as will be described in more detail hereinafter.

A second connecting portion or cup inserter 14 includes a body 32 and a handle 34. Handle 34 has a male, threaded end which is threadingly received within a female, threaded opening 38 in an extension 40 of body 32. Handle 34 includes a knob 42 which may be gripped by a user such that cup inserter 14 can be manipulated to a desired position. Body 32 can be provided in various sizes for use with various correspondingly sized cups 12.

Body 32 includes an end face 44 which is placed against annular face 22 of cup 12. End face 44 includes a plurality of fingers 46 extending therefrom. Each finger 46 is insertable into a corresponding one of notches 24 in cup 12. Fingers 46 are inserted into notches 24 by aligning fingers 46 with the respective notches 24 and moving body 32 in a direction parallel to longitudinal axis 20 toward cup 12. Each finger 46 includes a transverse surface 48 which matingly engages with a corresponding one of undercut walls 26 in each notch 24. The opening defined by each notch 24 in annular face 22 is large enough to accommodate the size of each corresponding finger 46, including the associated transverse surface 48. In the embodiment shown, each finger 46 has an L-shaped cross section and each transverse surface 48 extends substantially parallel to end face 44. However, it is also to be understood that fingers 46 may include a transverse surface which is disposed at an angle other than parallel to end face 44. For example, transverse surface 48 may be disposed at an acute angle relative to end face 44. Configured as such, undercut wall 26 of each notch 24 would likewise be disposed at a mating acute angle.

End face 44 includes a keying device in the form of a shoulder 50 which mates with elevation 30 on end face 22 of cup 12. Shoulder 50 and elevation 30 coact with each other such that cup inserter 14 may only be connected to cup 12 at one particular orientation. Of course, keying arrangements other than shoulder 50 and elevation 30 may be utilized. Moreover, depending upon the particular application, the interconnection between cup inserter 14 and cup 12 need not necessarily be keyed. For example, the outer face 22 of cup 12 may be substantially planar and thus not include an elevation 30, in which case, the mating end face 44 would not include corresponding shoulder 50.

Cup inserter 14 further includes a projection 52 and a biasing device 54 (FIG. 2). Projection 52 includes a cylindrical portion 56 and a head 58. Cylindrical portion 56 is slidingly disposed within a circular opening 60 formed in body 32. Projection 52 is movable within body 32 between a retracted position and an extended position, each of which will be described in further detail hereinafter. Biasing device 54 is configured as a compression spring in the embodiment shown in FIGS. 1 and 2. Spring 54 biases projection 52 toward the extended position, whereby head 58 is moved away from body 32.

A finger grip 62 is connected to an end of cylindrical portion 56 which extends through circular opening 60 and away from body 32. A collet 64 and set screw 66 engage an end of cylindrical portion 56 and prevent projection 52 from moving in an axial direction away from finger grip 62. Finger grip 62 includes a circular through-bore 68 through which cylindrical portion 56 of projection 52 extends. A small clearance is provided between through-bore 68 and cylindrical portion 56, whereby finger grip 62 may be moved in a rotational direction relative to projection 52, as indicated by rotational arrow 70.

Finger grip 62 also includes a V-shaped end 72 which is received within a corresponding V-shaped groove in body 32. Finger grip 62 is rotatable about axis 76 to a raised position wherein V-shaped end 72 is not disposed within V-shaped groove 74. When disposed out of V-shaped groove 74, V-shaped end 72 functions to hold finger grip 62 in the raised position whereby projection 52 is held in the retracted position with head 58 being substantially within body 32.

Referring now to FIGS. 3–6, a method of interconnecting cup inserter 14 with cup 12 will be described. Cup inserter 14 is shown without handle 34 in FIGS. 3–6 for purposes of simplicity. As will be appreciated, it is necessary to positively connect cup inserter 14 with cup 12 prior to inserting cup 12 in a prepared acetabulum of a patient, such that cup 12 may be properly positioned and oriented within the prepared acetabulum. Initially, cup inserter 14 is aligned with cup 12 such that fingers 46 align with respective notches 24. As shown in FIG. 3, each notch 24 is sized to allow a corresponding finger 46, including transverse surface 48 to be received therein. After fingers 46 are inserted into notches 24, as shown in FIG. 3, a downward force is applied against head 58 toward face 22 to retract head 58 into body 32, thus compressing spring 54. Body 32 is then rotated about longitudinal axis 20, whereby fingers 46 are moved to a locking position within the respective notches 24, as shown in FIG. 4. When each of fingers 46 is in the locking position, compression spring 54 biases head 58 of projection 52 into a projection receiving device formed in annular face 22 of cup 12. In the particular embodiment shown, the projection receiving device is defined by one of notches 24 in annular face 22. More specifically, head 58 of projection 52 is sized to fit within a portion of a notch 24 which is not occupied by a corresponding finger 46 when the finger 46 is in the locking position. Finger grip 62 is rotated to a position allowing V-shaped end 72 of finger grip 62 to be disposed within V-shaped groove 74 of body 32, thereby allowing compression spring 54 to move head 58 to the extended position such that head 58 of projection 52 is disposed within a notch 24. With the head 58 of projection 52 disposed in a notch 24, body 32 is prevented from rotating relative to cup 12, thereby locking cup inserter 14 with cup 12.

To disconnect cup inserter 14 from cup 12, finger grip 62 is moved in an axial direction away from body 32 under the force of compression spring 54. Finger grip 62 is then rotated approximately 90° in either direction such that V-shaped end 72 rests on top of body 32 and is disposed out of V-shaped groove 74 (FIG. 5). With finger grip 62 in the raised position, projection 52 is disposed in the retracted position whereby head 58 is not located within a notch 24. With finger grip 62 in the raised position, body 32 may be rotated about longitudinal axis 20 such that each finger 46 is moved to an unlocked position (FIG. 6). Cup inserter 14 may then be moved in an axial direction away from cup 12 to thereby disconnect cup inserter 14 from cup 12.

Referring now to FIGS. 7–9, there is shown another embodiment of an orthopaedic assembly 80 of the present invention, including an acetabular cup 82 and a cup inserter 84. Cup inserter 84 is shown without a handle for purposes of clarity. Cup 82 includes a cavity 86, pole 88, longitudinal axis 90, annular face 92 and fiber metal shell 94, similar to the embodiment of orthopaedic assembly 10 shown in FIGS. 1 and 2. However, annular face 92 includes a plurality of key hole shaped notches 96, with each notch 96 including an undercut wall 98. A projection receiving device in the form of an opening 100 is formed within each notch 96. Cup 82 does not include a keying device, such as an elevation or shoulder, in the embodiment shown in FIGS. 7–9.

Cup inserter 84 includes a body 102, end face 104, finger grip 106, biasing device 108 and projection 110, similar to the embodiment of cup inserter 14 shown in FIGS. 1 and 2. Cup inserter 84 also includes a plurality of fingers 112. However, fingers 112 have an enlarged head which is correspondingly received within a key hole shaped notch 96. More particularly, the enlarged head of each finger 112 is placed within the enlarged end of a corresponding notch 96 and force is applied against projection 110 to retract it, thus compressing biasing device 108. Body 102 is then rotated about longitudinal axis 90 such that the enlarged head is disposed adjacent to and engages undercut wall 98. Projection 110 snaps into place within an opening 100 when each of fingers 112 are rotated to the locking position behind undercut walls 98.

Finger grip 106 includes an end in the form of a nub 114 which is received within a corresponding small groove 116 in body 102. When nub 114 of finger grip 106 is positioned within groove 116, biasing device 108 can bias projection 110 to the extended position and into opening 100 (FIG. 8). On the other hand, when nub 114 of finger grip 106 is moved out of groove 116, biasing device 108 is compressed and projection 110 is moved to a retracted position within a corresponding finger 112 (FIG. 9).

With either of the embodiments of orthopaedic assembly 10 shown in FIGS. 1–8 or orthopaedic assembly 80 shown in FIGS. 7–9, the projections 52, 110 and biasing devices 54, 108 conjunctively provide an audible indication to a user that projections 52, 110 have been received within notch 24 or opening 100, respectively. Biasing device 54, 108 snaps projections 52, 110 into place when fingers 46, 112 are moved to the locking position, resulting in an audible clicking sound being heard by the user. The user thus is able to ascertain that cup inserter 14, 84 has positively locked with the acetabular cup 12, 82.

Inserters 14, 84 are preferably made of metal, such as stainless steel, although any suitable material may be used. Any suitable manufacturing method may be utilized.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic assembly, comprising:
    an acetabular cup including a cavity for receiving a femoral head and a pole defining a longitudinal axis through said cavity, said acetabular cup further including an annular face bounding said cavity, said annular face including a plurality of notches extending therein, each said notch including an undercut wall, said annular face further including a projection receiving means; and
    a cup inserter including a body with an end face and a plurality of fingers extending from said end face, each said finger being insertable into a corresponding one of said plurality of notches in a direction parallel to said longitudinal axis and rotatable around said longitudinal axis to a locking position, each said finger including a transverse surface which matingly engages with a corresponding one of said undercut walls when said finger is in said locking position, said cup inserter further including a projection and a biasing device, said projection slidably carried within said body and movable between a retracted position and an extended position, said biasing device comprising a resilient member for said projection toward said extended position, said projection being biased to said extended position and received within said projection receiving means of said cup when each said finger is in said locking position.

2. The orthopaedic assembly of claim 1, wherein one of said notches defines said projection receiving means.

3. The orthopaedic assembly of claim 1, wherein each of said notches and each of said fingers have an L-shaped cross section.

4. The orthopaedic assembly of claim 1, wherein each of said notches are keyhole shaped and each of said fingers have an enlarged head.

5. The orthopaedic assembly of claim 1, wherein said biasing device comprises a spring.

6. The orthopaedic assembly of claim 5, wherein said spring comprises a compression spring.

7. The orthopaedic assembly of claim 1, wherein said biasing device, said projection and said projection receiving means conjunctively define a means for providing an audible indication to a user that said projection is received within said projection receiving means.

8. The orthopaedic assembly of claim 7, wherein said audible indication comprises a clicking sound.

9. The orthopaedic assembly of claim 1, wherein said cup inserter further comprises a finger grip extending from said body, said finger grip coupled with each of said projection and said biasing device, said finger grip movable away from said body to thereby move said projection to said retracted position.

10. The orthopaedic assembly of claim 9, wherein said body includes a groove and said finger grip includes an end which is received within said groove, said finger grip being rotatable about an axis to a raised position wherein said end is not received within said groove, said projection being in said retracted position when said finger grip is in said raised position.

11. The orthopaedic assembly of claim 10, wherein said groove and said end of said finger grip each have a V-shape.

12. The orthopaedic assembly of claim 1, wherein said acetabular cup is comprised of a polymeric material.

13. The orthopaedic assembly of claim 12, wherein said acetabular cup further comprises a porous, metallic shell.

14. The orthopaedic assembly of claim 12, wherein said acetabular cup is comprised of ultra-high-molecular weight polyethylene.

15. The orthopaedic assembly of claim 1, wherein said annular face of said acetabular cup and said end face of said cup inserter each include mating keying devices for keyed interconnection between said acetabular cup and said cup inserter.

16. The orthopaedic assembly of claim 15, wherein said keying device of said annular face comprises an elevation, and wherein said keying device of said end face comprises a shoulder.

17. An orthopaedic assembly, comprising:
 a first portion defining a longitudinal axis, said first portion including an outer face, said outer face including a plurality of notches extending therein, each said notch including an undercut wall, said outer face further including a projection receiving means; and
 a second connecting portion including a body with an end face and a plurality of fingers extending from said end face, each said finger being insertable into a corresponding one of said plurality of notches in a direction parallel to said longitudinal axis and rotatable around said longitudinal axis to a locking position, each said finger including a transverse surface which matingly engages with a corresponding one of said undercut walls when said finger is in said locking position, said second connecting portion further including a projection and a biasing device, said projection slidably carried within said body and movable between a retracted position and an extended position, said biasing device comprising a resilient member for said projection toward said extended position, said projection being biased to said extended position and received within said projection receiving means of said first portion when each said finger is in said locking position.

* * * * *